(12) United States Patent
Frick et al.

(10) Patent No.: US 8,701,666 B2
(45) Date of Patent: Apr. 22, 2014

(54) ADAPTER FOR CONNECTING PARTICULARLY A RESPIRATORY IMPLEMENT TO A TUBE

(75) Inventors: Ulrich Frick, Weinstadt (DE); Albrecht Kauffmann, Weinstadt (DE)

(73) Assignee: Medilone Medical Grosshandels GmbH, Waiblingen-Neustadt (DE)

( * ) Notice: Subject to any disclaimer, the term of this patent is extended or adjusted under 35 U.S.C. 154(b) by 337 days.

(21) Appl. No.: 12/739,817

(22) PCT Filed: Oct. 23, 2008

(86) PCT No.: PCT/EP2008/008981
§ 371 (c)(1),
(2), (4) Date: May 27, 2010

(87) PCT Pub. No.: WO2009/053074
PCT Pub. Date: Apr. 30, 2009

(65) Prior Publication Data
US 2010/0252045 A1      Oct. 7, 2010

(30) Foreign Application Priority Data

Oct. 25, 2007   (DE) .......................... 10 2007 050 974

(51) Int. Cl.
*A61M 16/08* (2006.01)
(52) U.S. Cl.
USPC ............ 128/205.12; 128/204.18; 128/205.13
(58) Field of Classification Search
USPC ............ 128/205.13, 205.12, 204.12, 204.18, 128/13, 14, 202.27, 205.24, 207.14–16, 128/912; 220/784, 305, 298, 293, 790, 794, 220/321, 819; 215/216; 285/242
See application file for complete search history.

(56) References Cited

U.S. PATENT DOCUMENTS

| | | | |
|---|---|---|---|
| 3,133,777 A | | 5/1964 | Anhalt |
| 3,802,607 A | * | 4/1974 | Mead ............................ 222/182 |
| 4,729,765 A | | 3/1988 | Eckels et al. |
| 2008/0041391 A1 | | 2/2008 | Worley |

FOREIGN PATENT DOCUMENTS

| | | |
|---|---|---|
| DE | 1440918 A1 | 12/1968 |
| DE | 295 17 416 U1 | 12/1995 |
| DE | 195 43 169 C2 | 11/1996 |
| DE | 297 03 339 U1 | 6/1997 |
| WO | 2007092199 A2 | 8/2007 |

* cited by examiner

*Primary Examiner* — Jackie Ho
*Assistant Examiner* — Mark Wardas
(74) *Attorney, Agent, or Firm* — Laurence A. Greenberg; Werner H. Stemer; Ralph E. Locher

(57) ABSTRACT

An adapter for connecting, in particular, respiratory implements such as tubes, tube extensions, filters, breather bags, or artificial noses to a tube having a particularly conically tapered connector. the adapter has a clamping section that may be fixed to the connector in a frictionally engaged manner. The clamping section of the adapter may be radially expanded from a first clamping position in which the inner diameter of the clamping section is less than the outer diameter of the connector into a second release position in which the inner diameter of the clamping section is greater than the outer diameter of the connector.

10 Claims, 4 Drawing Sheets

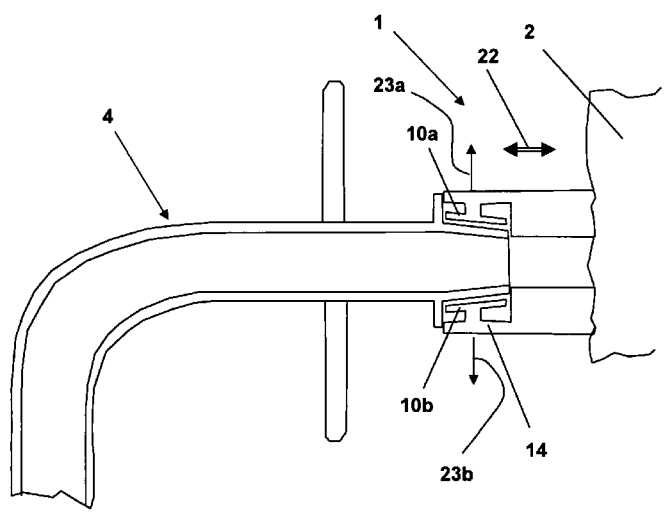
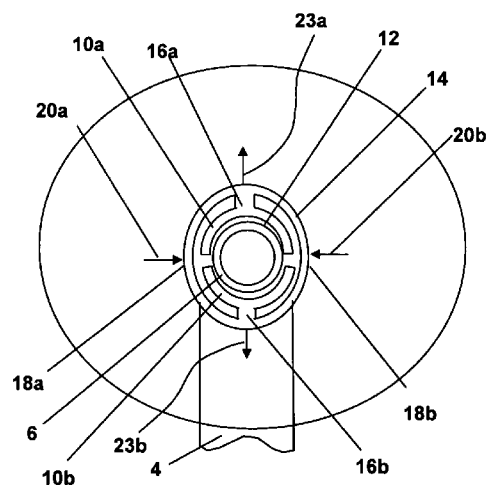
FIG. 2A
FIG. 2B

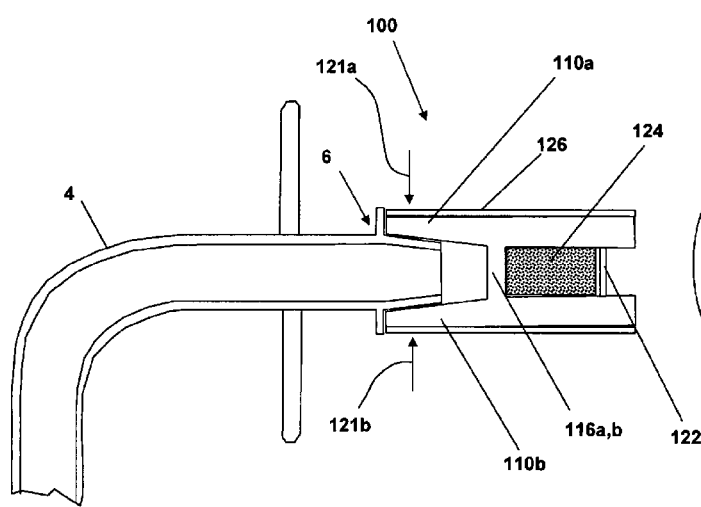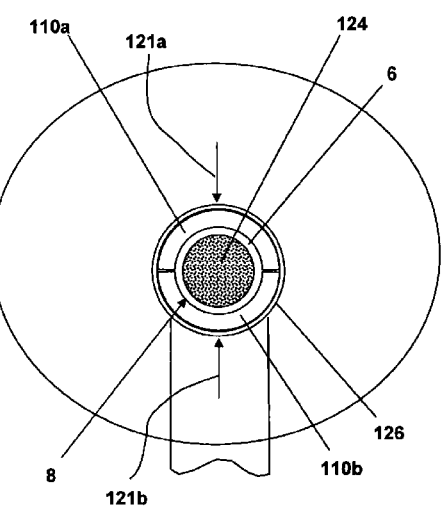
FIG. 3A
FIG. 3B

ADAPTER FOR CONNECTING PARTICULARLY A RESPIRATORY IMPLEMENT TO A TUBE

BACKGROUND OF THE INVENTION

Field of the Invention

The invention relates to an adapter for connecting particularly a respiratory implement, such as a flexible tube, a tube extension, a respiratory air filter, a respiration bag or an artificial nose or the like, to a tube which is insertable into the human body, with a preferably conically tapering connector, in accordance with the precharacterizing clause of clause 1.

The problem with the known connecting adapters, with which the abovementioned respiratory air supply or preparation devices—which are referred to below as respiratory implements for the sake of simplicity—can be connected to tube connectors is that, after being plugged together, the connector bearing surfaces, which generally converge in a slightly conical manner, require comparatively high breakaway torques because of the adhesion behavior of the plastics material and the conicity of the contact surfaces in order to release the clamping connection, which seals in a frictionally engaged manner, again.

Said comparatively high forces and torques which have to be overcome in order to release the connection between the adapter and connector give rise to the problem of, for example, a tracheal tube which is inserted into a patient's neck region frequently being moved inadvertently in the neck region, which may cause pain and, over time, even injuries to the patient.

BRIEF SUMMARY OF THE INVENTION

Accordingly, it is an object of the invention to provide an adapter for connecting in particular respiratory implements to the connector of a tube which is insertable into the human body, in which the sealing clamping connection between the adapter and connector can be released without torques or tensile forces being applied to the tube.

This object is achieved according to the invention in that the adapter comprises a clamping section which is fixable to the connector in a frictionally engaged manner and which is expandable from a first clamping position, in which the inside diameter of the clamping section is smaller than the outside diameter of the connector, radially into a second release position, in which the inside diameter of the clamping section is larger than the outside diameter of the connector, by application of a compressive force acting on the clamping section.

The term tube which is used below for linguistic simplification is to be understood here as in general meaning flexible medicinal tubes or tubular objects—such as, for example, tracheal tubes, tracheal cannulas or even infusion cannulas etc.—which are inserted at least temporarily into the human body in order to supply respiratory air, liquids, medicaments or appliances, such an endoscopes or the like, to a patient or to remove body fluids from the patient.

The invention gives rise to the advantage that in particular the abovementioned respiratory implements can be connected within a very short period of time, even by untrained personnel, to a tube, for example a tracheal cannula or a tracheal tube, inserted into the human body and can be removed therefrom again without causing significant stress to the patient.

According to a preferred refinement of the invention, the connecting adapter comprises an outer sleeve-like section which is designed, for example, as a sleeve made of plastics material, for example polyethylene, and can have a wall thickness of, for example, 1 mm to 2 mm. The flexibility of the material is selected here in a manner according to the invention such that said section, which is annular, as viewed in cross section, can be deformed to form an oval by compression with the thumb and index finger in the region of two compressive surfaces provided diametrically on the outer side of the section.

A respective connecting element which may be, for example, in the shape of a web extending radially inward is arranged, preferably on the inner surface of the outer circumferential surface of the sleeve-like section, preferably perpendicularly, i.e. rotated through 90°, with respect to the engagement points of the compressive force. The radially inner ends of the connecting elements are each provided with a half-shell-like section which has a semi-annular shape in cross section.

When observed together, the two half-shell-like sections are in the shape of a sleeve divided centrally in the longitudinal direction, or of a truncated cone, the inner surface of which is matched to the shape of the outer surface of the connector such that the clamping section which is defined by the half-shell-like sections and is annular in cross section has a slightly smaller inside diameter than the outside diameter of the connector when a compressive force is not being exerted on the outer sleeve-like section. In this case, the bearing force with which the two half-shell-like sections are pressed against the outer surface of the connector is preferably produced solely by the inherent stiffness of the flexible material of the outer sleeve-like section.

If the outer half-shell-like section, which is preferably in the cross-sectional shape of a ring, is deformed into an oval by means of an external, diametrically acting compressive force, the two half-shell-like sections, actuated via the webs, move, for example, by 1 to 2 mm radially outward and thereby expand the distance between the inner surfaces of the two half-shell-like sections, as a result of which the sealing clamping connection between the half-shell sections and the outer surface of the connector is released and the adapter together with the associated respiratory implement can be pulled off from the connector.

In order to plug the adapter with the, for example, respiratory implement arranged thereon onto the connector, the outer sleeve-like section is first of all diametrically compressed with the thumb and index finger, as a result of which the outer sleeve-like section is deformed in cross section to form an oval and the inner surfaces of the two half-shell-like sections are moved away from each other. The adapter is then pushed in the axial direction onto the connector and the compressive force released, as a result of which the outer sleeve-like section, owing to the inherent elasticity of the material, is moved back into its starting position, in which it is annular in cross section, and the inner surfaces of the two half-shell-like sections are moved via the connecting elements against the outer surface of the connector and clamp said outer surface in a sealing manner.

According to a further embodiment of the invention, the clamping section of the connector adapter comprises two half shells or half-shell-like sections having a length of, for example, 3-4 cm, which are connected approximately in their center via elastic webs arranged on both sides. The two webs here define a pivot axis which has the effect that that part of the expandable section which faces the connector is expanded in the manner of a duckbill when a compressive force pressing the half shells against each other is exerted on the other side of the webs on that side of the two half shells which faces away from the connector.

According to a development of this embodiment of the invention, a further spring-elastic element can be provided in order to increase the clamping force in the region of the end facing away from the connector, said element acting between the two half-shell-like sections and forcing the latter apart. In this case, the spring-elastic element is preferably designed as an additional web made of elastic material which ensures in an advantageous manner that, when the adapter is used in conjunction with an artificial nose, the foam filter for remoistening the inhaled respiratory air is fixed in its position.

In order, in the case of the last-described embodiment of the invention, to seal the two half-shell-like sections in the clamping position against an escape of respiratory air, the two half-shell-like sections can furthermore be provided in the region of the laterally remaining slots with sealing means, for example inner sealing lips, or with a covering made of flexible material, which covering can consist, for example, of a thin-walled elastic plastics material or an elastic film.

The invention is described by way of example below with reference to the drawings and using two preferred embodiments in conjunction with a tube in the form of a tracheal cannula.

BRIEF DESCRIPTION OF THE SEVERAL VIEWS OF THE DRAWING

FIG. 2b shows a partially transparent front view of the adapter from FIG. 2a, FIG. 3a shows a schematic lateral cross-sectional view of a tracheal cannula with an attached adapter according to a further embodiment of the invention in the clamping position, FIG. 3b shows a partially transparent front view of the adapter from FIG. 3a, FIG. 4a shows a schematic lateral cross-sectional view of the tracheal cannula with the attached adapter according to the second embodiment in the release position, and FIG. 4b shows a partially transparent front view of the adapter from FIG. 4a.

DESCRIPTION OF THE INVENTION

Figures 1A, 1B:
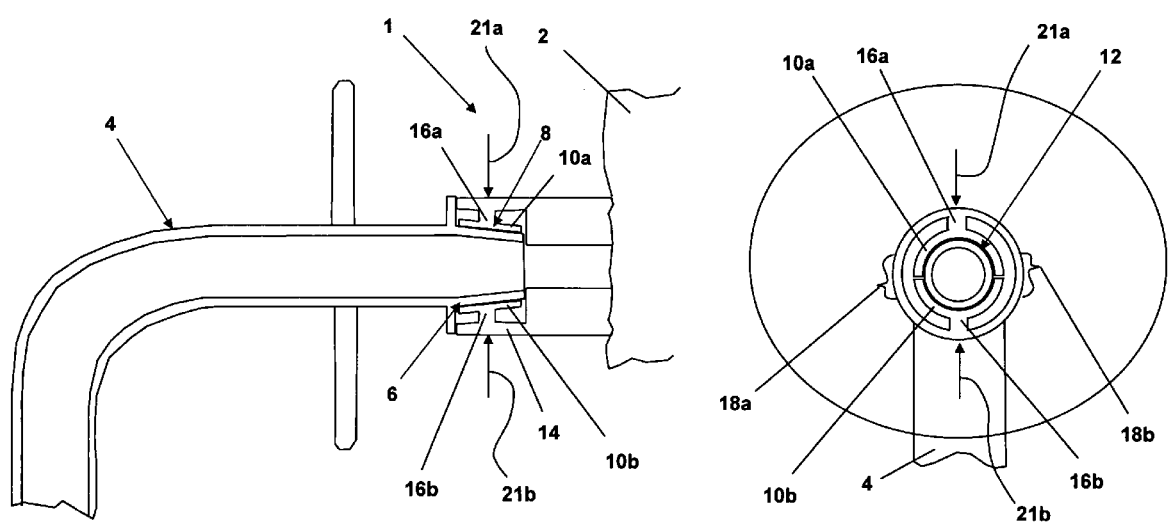
FIG. 1a shows a schematic lateral cross-sectional view of a tracheal cannula with an attached adapter according to a first embodiment of the invention in the clamping position.
FIG. 1b shows a partially transparent front view of the adapter of FIG. 1a, FIG. 2a shows a schematic lateral cross-sectional view of the tracheal cannula with the attached adapter according to the first embodiment in the release position.

As FIGS. 1a and 1b show, an adapter 1 according to the invention for connecting respiratory implements 2 (merely indicated schematically in the drawings), such as flexible tubes, tube extensions, filters, respiration bags or artificial noses etc., to a tube in the form of a tracheal cannula 4, which is shown by way of example and has a conically tapering connector 6, comprises a clamping section 8 which can be expanded radially from the first clamping position shown in FIGS. 1a, 1b—in which the inside diameter of the clamping section 8 is smaller than the outside diameter of the connector 6—into a second release position shown in FIGS. 2a, 2b by application of a compressive force acting on the clamping section 8.

As shown in detail in FIGS. 1a and 1b, the clamping section 8 comprises a first and second half-shell-like section 10a, 10b which, in the first clamping position, bears against the outer surface 12 of the connector 6 forming a substantially annular cross section. In this case, the half-shell-like sections 10a, 10b are located within an outer sleeve-like section 14 of flexible material, with which said sections are connected via a first and second connecting element in the form of a connecting web 16a, 16b. The clamping force which is indicated by the two arrows 21a and 21b and with which the half-shell-like sections 10a, 10b bear under prestress against the connector 6 is produced here by the inherent elasticity of the material.

Each of the two connecting webs 16a, 16b which are preferably formed integrally with the outer sleeve-like section 14 originates in a manner according to the invention in the region of the inner surface of the outer sleeve-like section 14 at a position which is arranged offset by 90° with respect to a compressive surface 18a, 18b provided on the outer side of the outer sleeve-like section 14, said connecting web extending radially inward therefrom.

As can be seen with reference to the cross-sectional illustration of FIG. 2b, the outer sleeve-like section 14 is deformed diametrically to form an oval by application of a compressive force, which is indicated by the arrows 20a, 20b and can be applied, for example, by the thumb and the index finger of a human hand, this resulting in the half-shell-like sections 10a and 10b being moved away from each other via the connecting webs 16a, 16b in the direction of the arrows 23a and 23b, as a result of which the clamping connection is released. In this position of the half-shell-like sections 10a, 10b, the adapter 1 can then be pulled off in the direction of the arrow 22 from the connector 6 or plugged onto the latter, as indicated in FIG. 2a.

As illustrated in FIGS. 3a, 3b and 4a, 4b, it can be provided according to a further embodiment of the invention that the adapter, which is referred to in this case by the reference number 100, has a first and second half-shell-like section 110a and 110b, which sections are connected to each other via elastic webs 116a, 116b.

Figures 4A, 4B:
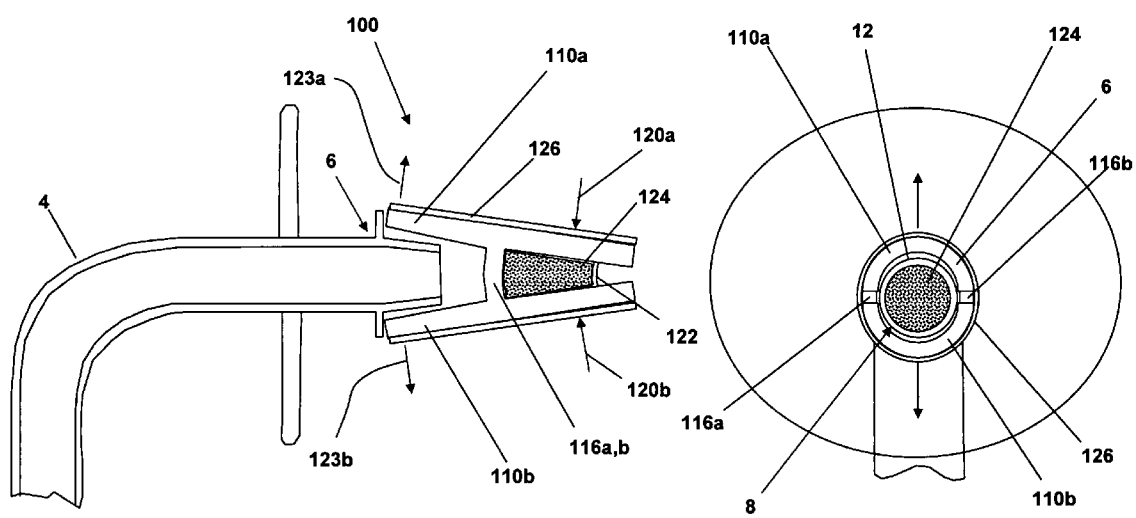

As can furthermore be gathered from the illustration of FIGS. 4a and 4b, the inherent elasticity of the two webs 116a, 116b means that they define a type of pivot axis which has the effect that that part of the expandable section or clamping section 8 which faces the connector 6 expands in the manner of a duckbill when a compressive force, indicated by the arrows 120a, 120b, is exerted on the other side of the two webs 116a, 116b on that side of the two half-shell-like sections 110a and 110b which faces away from the connector 6. By means of said compressive force, the two half-shell-like sections 110a and 110b, which, according to the illustration of FIGS. 3a and 3b, bear in the clamping position under prestress against the connector 6 with a clamping force which is indicated by the arrows 121a and 121b, are moved away from the connector 6 in the direction of the arrows 123a and 123b.

According to a development of this embodiment of the invention, in order to increase the clamping force, an additional spring-elastic element 122 can be provided in the region of the end facing away from the connector 6, said element producing a compressive force between the two half-shell-like sections 110a and 110b, said compressive force pushing the sections 110a and 110b apart. In this case, the spring-elastic element 122 is preferably designed as an additional web made of elastic material ensuring in an advantageous manner that, when the adapter 100 is used in conjunction with an artificial nose, which is likewise indicated in FIGS. 3 and 4, the foam filter 124 for the remoistening of the inhaled air remains in its position.

The adapter 1, 100 according to the invention together with its associated components is preferably manufactured in one piece, in particular as injection molded part, although it can likewise be provided that the adapter 1, 100 is composed of a plurality of individual components. For example, it is conceivable that the adapter 100 which is shown in FIGS. 3 and 4 is obtained by retrospective slitting of a plastic sleeve which is cut to the desired length and, in order to seal the slot, can be provided in the region of the connector 6 with corresponding sealing elements, such as sealing lips or a covering 126 which is indicated in FIGS. 3 and 4 and is preferably composed of a flexible, for example, rubbery material.

Although the invention has been described above with reference to a male connector 6 in conjunction with a female adapter 1, 100 which is preferably arranged directly on a respiratory implement 2, it goes without saying that the concept on which the invention is based is also applicable to the reverse configuration comprising a male adapter and a female connector.

List of Reference Numbers

1 connecting adapter according to the invention
2 respiratory implement
4 tracheal cannula
6 connector
8 clamping section
10a first half-shell-like section
10b second half-shell-like section
12 outer surface of the connector
14 outer sleeve-like section
16a first connecting web
16b second connecting web
18a first compressive surface
18b second compressive surface
20a arrow
20b arrow
21a arrow which indicates clamping force
21b arrow which indicates clamping force
22 arrow
23a arrow which indicates the movement of the first half-shell-like section upon release of the clamping force
23b arrow which indicates the movement of the second half-shell-like section upon release of the clamping force
100 adapter
110a first half-shell-like section
110b second half-shell-like section
116a first elastic web
116b second elastic web
120a arrow
120b arrow
121a arrow which indicates clamping force
121b arrow which indicates clamping force
122 spring elastic element
123a arrow which indicates the movement of the first half-shell-like section upon release of the clamping force
123b arrow which indicates the movement of the second half-shell-like section upon release of the clamping force
124 foam filter
126 covering

The invention claimed is:

1. An adapter for connecting a respiratory implement to a tube, the tube being formed with a connector having a conically tapering outside diameter, the adapter comprising:
a clamping section having first and second half-shell sections each having a respective conically tapering inner surface, said conically tapering inner surfaces being matched to the outside diameter of the connector, said clamping section being constructed for radially expanding from a clamping position, in which said conically tapering inner surfaces of said clamping section are frictionally engaged against the conically tapering outside diameter for holding said clamping section in place on the connector in a sealing connection, into a release position, in which said conically tapering inner surfaces are released from frictional engagement and spaced from the conically tapering outside diameter of the connector, on being subjected to a compressive force acting on said clamping section, and said clamping section being defined by first and second half-shell sections in the shape of a sleeve divided centrally along a longitudinal axis thereof and over an entire length of said sleeve.

2. An adapter for connecting a respiratory implement to a tube, the tube being formed with a connector having a conically tapering outer surface with a defined outside diameter, the adapter comprising:
a clamping section to be affixed to the connector in frictional engagement therewith;
said clamping section being formed to radially expand from a first clamping position, in which an inside diameter of said clamping section is smaller than the outside diameter of the connector, into a second release position, in which the inside diameter of said clamping section is greater than the outside diameter of the connector, on being subjected to a compressive force acting on said clamping section;
said clamping section being defined by first and second half-shell sections in the shape of a sleeve divided centrally along a longitudinal axis thereof and over an entire length of said sleeve, said half-shell sections each having a respective inner surface being matched to the outer surface of the connector, and in the first clamping position, said first and second half-shell sections bear against the outer surface of the connector in a sealing and clamping connection, and, in the second release position, the first and second half-shell sections being spaced with a spacing distance from the outer surface of the connector for release of the clamping connection.

3. The adapter according to claim 2, wherein said half-shell sections are arranged within an outer sleeve section of flexible material, and wherein at least one of said half-shell sections is connected to said outer sleeve section via a connecting element in such a manner that said half-shell sections are moved away from each other upon action of a compressive force on said outer sleeve section.

4. The adapter according to claim 3, wherein said half-shell sections are two sections respectively coupled to an outer sleeve section via a web extending radially inward within the outer sleeve section, and each of said webs is disposed offset by 90° with respect to a first and second compressive surface, respectively, which is provided diametrically on an outer side of said outer sleeve section and via which said outer sleeve section can be deformed.

5. An assembly, comprising a tube and an adapter according to claim 2.

6. The assembly according to claim 5, comprising a respiratory implement selected from the group consisting of a flexible respirator tube, a tube extension, a respiratory air filter, a respiration bag, and an artificial nose to be connected by way of said adapter.

7. An adapter for connecting a respiratory implement to a tube, the tube being formed with a connector having a conically tapering outer surface with a defined outside diameter, the adapter comprising:
- a clamping section to be affixed to the connector in frictional engagement therewith;
- said clamping section being formed to radially expand from a first clamping position, in which an inside diameter of said clamping section is smaller than the outside diameter of the connector, into a second release position, in which the inside diameter of said clamping section is greater than the outside diameter of the connector, on being subjected to a compressive force acting on said clamping section;
- said clamping section being defined by first and second half-shell sections in the shape of a sleeve divided centrally along a longitudinal axis thereof, said half-shell sections each having a respective inner surface being matched to the outer surface of the connector, and in the first clamping position, said first and second half-shell sections bear against the outer surface of the connector in a sealing and clamping connection, and, in the second release position, the first and second half-shell sections being spaced with a spacing distance from the outer surface of the connector for release of the clamping connection;
- said first and second half-shell sections being connected via elastic webs disposed on both sides and defining a pivot axis, such that those parts of said first and second half-shell sections that face the connector are pivoted away from each other from the first clamping position into the second release position when said half-shell sections are acted upon with a compressive force in a region of their ends opposite the connector.

8. The adapter according to claim 7, which comprises a spring-elastic element acting between said first and second half-shell sections disposed at an end facing away from the connector.

9. The adapter according to claim 7, which comprises sealing means disposed to seal said half-shell sections against an escape of respiratory air.

10. The adapter according to claim 9, wherein said sealing means are a flexible covering.

* * * * *